(12) United States Patent
Epstein

(10) Patent No.: US 10,441,482 B2
(45) Date of Patent: Oct. 15, 2019

(54) SOILED UNDERGARMENT DISPOSAL CONTAINER

(71) Applicant: Tomer Epstein, Côte-Saint-Luc (CA)

(72) Inventor: Tomer Epstein, Côte-Saint-Luc (CA)

(73) Assignee: Tomer Epstein, Côte-Saint-Luc (CA)

(*) Notice: Subject to any disclaimer, the term of this patent is extended or adjusted under 35 U.S.C. 154(b) by 258 days.

(21) Appl. No.: 15/481,010

(22) Filed: Apr. 6, 2017

(65) Prior Publication Data
US 2017/0290719 A1    Oct. 12, 2017

Related U.S. Application Data

(60) Provisional application No. 62/318,814, filed on Apr. 6, 2016.

(51) Int. Cl.
| | |
|---|---|
| *A61F 13/551* | (2006.01) |
| *A61F 13/496* | (2006.01) |
| *A61F 13/84* | (2006.01) |
| *A61M 39/24* | (2006.01) |

(52) U.S. Cl.
CPC ........ *A61F 13/5512* (2013.01); *A61F 13/496* (2013.01); *A61F 13/84* (2013.01); *A61M 39/24* (2013.01); *A61F 2013/55195* (2013.01); *A61F 2013/8402* (2013.01)

(58) Field of Classification Search
CPC .... B65D 33/01; A61F 13/5512; A61F 13/496; A61F 13/84; A61M 39/24
USPC ....................................... 383/2, 103, 88, 89
See application file for complete search history.

(56) References Cited

U.S. PATENT DOCUMENTS

| | | | |
|---|---|---|---|
| 3,806,984 A | 4/1974 | Hilsabeck | |
| 5,275,490 A | 1/1994 | Loebbert | |
| 6,164,821 A | 12/2000 | Randall | |
| 6,227,706 B1 * | 5/2001 | Tran ....................... | A45C 13/02 |
| | | | 206/524.8 |
| 6,983,845 B2 * | 1/2006 | Shah ....................... | B65D 33/01 |
| | | | 206/524.8 |
| 7,004,632 B2 * | 2/2006 | Hamilton ................ | B65D 33/01 |
| | | | 383/100 |
| 7,344,022 B2 * | 3/2008 | Madson .................. | B65D 33/25 |
| | | | 206/205 |
| 2004/0000501 A1 * | 1/2004 | Shah ....................... | B65D 33/01 |
| | | | 206/524.8 |

(Continued)

FOREIGN PATENT DOCUMENTS

CN          103482197 A     1/2014

*Primary Examiner* — Jes F Pascua
(74) *Attorney, Agent, or Firm* — Thomas | Horstemeyer, LLP

(57) ABSTRACT

A soiled undergarment disposal container is provided. The soiled undergarment disposal container includes a bag for housing a soiled undergarment and a sealable closure for sealing the bag. A resizing mechanism including a one-way degassing valve is provided to extract air from the bag, when sealed, upon application of a force on the bag by a user, and a plurality of studs each sized and shaped to fit into and close an air extraction aperture of the one-way degassing valve. The position and shape of the studs provides multiple sizing options for securing the folded or rolled sealed bag containing different soiled undergarment products. The bag in a compact state is configured for concealed transport of the soiled undergarment under or within a user's clothing, and/or within a user's handbag, purse, bag.

12 Claims, 5 Drawing Sheets

(56) References Cited

U.S. PATENT DOCUMENTS

| | | |
|---|---|---|
| 2005/0031228 A1* | 2/2005 | Galomb .............. B65D 33/25 383/96 |
| 2005/0228354 A1 | 10/2005 | Scholer |
| 2005/0267432 A1 | 12/2005 | Sundberg et al. |
| 2012/0059345 A1 | 3/2012 | Dayton et al. |
| 2013/0220226 A1 | 8/2013 | Molzan |
| 2014/0233872 A1 | 8/2014 | Stark et al. |

* cited by examiner

SOILED UNDERGARMENT DISPOSAL CONTAINER

FIELD OF THE INVENTION

The invention generally relates to the discreet disposal of soiled undergarments or the like. More specifically, the present invention relates to a soiled undergarment disposal container.

BACKGROUND

Recently, many improvements have been made in the development of disposable undergarments, including but not limited to underwear, adjustable briefs, diapers, absorbing pads, tampons, male hygiene products, and female hygiene products. The undergarments' appearance, softness, absorbency, fit, size and shape have all been improved in many different ways.

However, disposal of soiled undergarments still remains a problem with respect to hygiene, smell and disposal. Some efforts towards improving undergarment disposal appear in patent documents. However, few of these documents address how to properly conceal a soiled undergarment after use thereof. There is a need for a concealment solution that can help avoid displaying that the user has recourse to the use of disposable undergarments, and the embarrassments this may cause in public places.

Therefore, there is presently a need for a soiled undergarment concealment system that can address at least one of the above-mentioned problems.

SUMMARY

The object of the present invention is to provide a soiled undergarment disposal container, which by virtue of its design and components, satisfies some of the above-mentioned needs and is thus an improvement over other related soiled undergarment disposal containers and/or methods known in the prior art, or other similar applications.

In accordance with the one aspect, there is provided a disposal container for concealing a soiled undergarment. The disposal container includes a bag having opposite side walls and a top opening for inserting the soiled undergarment in the bag therethrough. The top opening of the bag provided with a sealable closure for sealing the bag with the soiled undergarment contained therein. The disposal container further includes a resizing mechanism which includes:
  a one-way degassing valve mounted through a first one of the side walls of the bag, the one-way degassing valve having an air extraction aperture configured to extract air from the bag, when sealed, upon application of a force on the bag by a user; and
  a plurality of studs each sized and shaped to fit into and close the air extraction aperture of the one-way degassing valve, each stud of the plurality of studs being positioned on one of the side walls at a different distance from the top opening of the bag.

According to one embodiment, the one-way degassing valve and the plurality of studs are respectively positioned on opposite side walls of the bag.

According to one embodiment, the one-way degassing valve and the plurality of studs are positioned on a same side wall of the bag.

According to another embodiment, the studs are positioned along a straight line perpendicular to the top opening of the bag.

According to one embodiment, the plurality of studs comprises between 2 and 10 of said studs.

According to yet another embodiment, the studs are equally spaced from one another.

According to one embodiment, the side walls of the bag have a rectangular shape.

According to one embodiment, the side walls of the bag are shaped as a mitten.

According to one embodiment, the air extraction aperture and the studs are configured so that the insertion of one of the studs into the aperture produces an audible clicking sound.

According to one embodiment, the bag includes an adhesive-covered plastic overlap foldable over the sealable closure of the bag.

According to one embodiment, the bag is made of a disposable material.

According to one embodiment, the bag is made of polyethylene.

Other features and advantages of the invention will be better understood upon a reading of embodiments thereof with reference to the appended drawings.

DETAILED DESCRIPTION

In the following description, the same numerical references refer to similar elements. The embodiments, geometrical configurations, materials mentioned and/or dimensions shown in the figures or described in the present description are preferred embodiments only, given for exemplification purposes only.

Moreover, although the container described herein was primarily designed for soiled undergarments, it may be used for other types of purposes and with other types of objects, and in other fields, as apparent to a person skilled in the art. For this reason, expressions such as "soiled undergarment", etc., used herein should not be taken as to limit the scope of the present invention and includes all other kinds of objects or fields with which the present invention could be used and may be useful.

In addition, although the embodiments of the present invention as illustrated in the accompanying drawing may comprise various components, and although the embodiments of the soiled undergarment disposal container as shown consists of certain configurations as explained and illustrated herein, not all of these components are essential to the invention and thus should not be taken in their restrictive sense, i.e. should not be taken as to limit the scope of the present invention. It is to be understood, as also apparent to a person skilled in the art, that other suitable components and cooperation thereinbetween, as well as other suitable configurations may be used for the soiled undergarment disposal container and corresponding components according to the present invention, as will be briefly explained hereinafter and as can be easily inferred herefrom by a person skilled in the art, without departing from the scope of the invention.

Figure 1A:
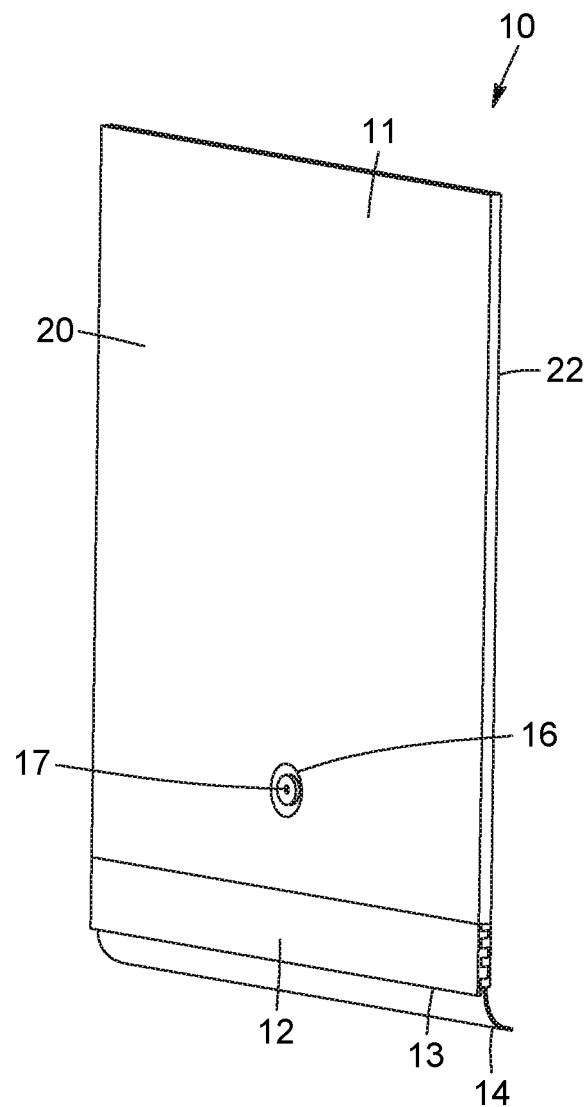
FIG. 1A is a perspective view of the front of the disposal container according to an embodiment of the present invention.
Figure 1B:
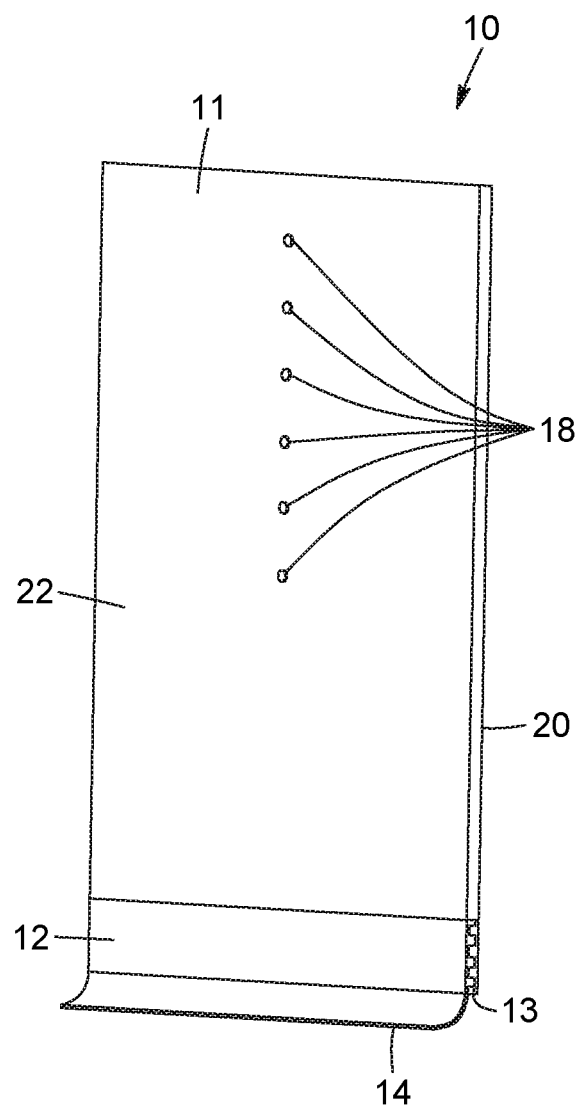
FIG. 1B is a perspective view of the back of the disposal container shown in FIG. 1A.

Referring to FIGS. 1A and 1B, there is shown a disposal container 10 according to one embodiment of the invention.

The disposal container 10 can be used to conceal a soiled undergarment (not shown). For example, the soiled undergarment may be underwear, disposable underwear, adjustable briefs, diapers, absorbing pads, tampons, feminine or male hygiene products, etc.

The disposal container includes a bag 11. The bag has opposite side walls 20, 22 and a top opening 13 for inserting the soiled undergarment in the bag 11 therethrough. The top opening 13 is provided with a sealable closure 12 for sealing the bag 11 with the soiled undergarment contained therein. The sealable closure 12 can for example include a triple zip lock closing mechanism or similar locking mechanism.

Figure 3A:
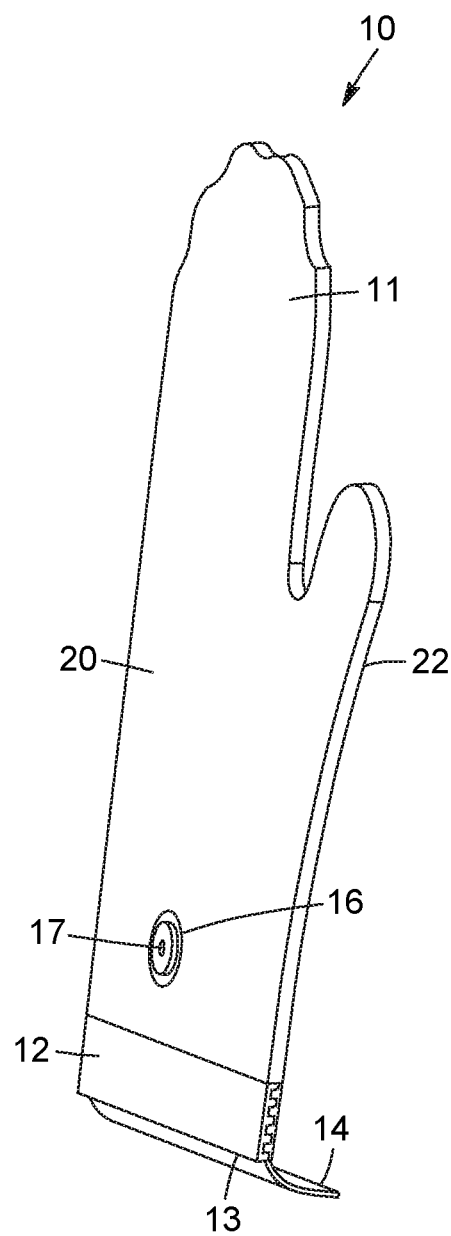
FIG. 3A is a perspective view of the front of the disposal container according to an embodiment of the present invention.
Figure 3B:
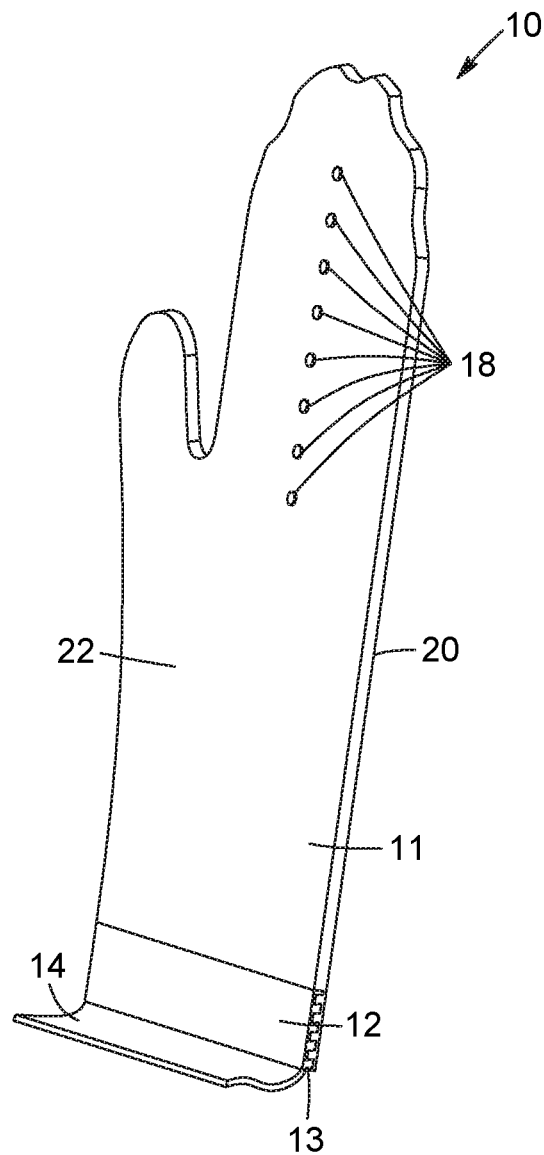
FIG. 3B is a perspective view of the back of the disposal container shown in FIG. 3A.

In the illustrated embodiment of FIGS. 1A and 1B, the side walls 20, 22 of the bag have a rectangular shape. In another embodiment and as shown on FIGS. 3A and 3B, the side walls 20, 22 of the bag are shaped as a mitten. However, as will be readily understood by one skilled in the art in other implementations the side walls 20, 22 of the bag can have any one of a variety of other shapes without departing from the scope of the invention.

In one variant (not shown), the bag may include an inner pouch housed within the bag for receiving the soiled undergarment. The inner pouch is removable from the bag for disposal and the bag may be kept for future use for which a new pouch is inserted within the bag. The bag and the inner pouch thus provide a reusable solution to conceal and dispose of a soiled undergarment. Alternatively, the bag can be a single-use solution and be completely disposable after a single use.

The bag 11 may additionally include odour suppression means for minimizing odours emanating from the soiled undergarment. In some embodiments, the bag 11 can be made of a disposable material, such as for example polyethylene or air-impermeable materials to minimize odours. It is to be understood, as also apparent to a person skilled in the art, that the bag can be made of any polymer material that is flexible and disposable such as nitrile, rubber material, or the like. In one embodiment, the bag 11 includes an adhesive-covered plastic overlap 14 foldable over the sealable closure of the bag to seal any possible remaining opening of the bag and reduce odours, as shown on FIG. 1B.

The disposal container further includes a resizing mechanism 24. The resizing mechanism 24 advantageously allows a user to easily conceal the soiled undergarment and hold the undergarment in a reduced volume before disposal as described below. This facilitates the concealed transport of the soiled undergarment which can be put into a handbag, a purse, a bag or under a user's clothing for example.

Referring now to FIG. 1A, in the illustrated embodiment the resizing mechanism 24 includes a one-way degassing valve 16. The one-way degassing valve 16 is mounted through a side wall 20 of the bag 11. The one-way degassing valve is for example made out of polymer material and is of the type that is commercially available for packaging products that require release of gas or excess air such as food products, agricultural products, or resin for example. The one-way degassing valve 16 has an air extraction aperture 17 configured to extract air from the bag 11, when sealed, upon application of a force on the bag 11 by a user.

As shown on FIG. 1B, the resizing mechanism 24 further includes a plurality of studs 18. The studs 18 may for example be made of plastic. Each stud 18 is sized and shaped to fit into and close the air extraction aperture 17 of the one-way degassing valve 16. In use, after the soiled undergarment has been inserted within the bag 11 and the bag 11 has been sealed using the sealable closure 12, a user can apply force on the bag 11 to extract air from the bag through the air extraction aperture 17 as described above. Once the bag 11 is in a sufficiently dry state or in a vacuum state, the user can fold or roll the bag 11 upon itself in the desired size or volume and insert one of the plurality of studs into the air extraction aperture to close it. The air extraction aperture 17 and the studs 18 may be configured so that the insertion of one of the studs 18 into the aperture 17 produces an audible clicking sound, therefore indicating that the bag 11 is safely sealed.

The bag 11 is thus maintained in a reduced volume and air-sealed. The bag 11 can be folded or rolled upon itself according to the size of the soiled undergarment.

In an embodiment, the bag 11 dissolves or otherwise chemically modifies the soiled undergarment before folding or rolling the bag 11 in a compact state.

As shown on FIG. 1B, each stud of the plurality of studs 18 is positioned on one of the side walls 22 at a different distance from the top opening 13 of the bag 11 in order to provide multiple sizing options for the different soiled undergarment products listed above. By way of example, in the illustrated embodiment of FIG. 1B the studs 18 are positioned along a straight line perpendicular to the top opening 13 of the bag and 11 may be equally spaced from one another. The plurality of studs 18 may for example include between 2 and 10 studs.

Figure 2:
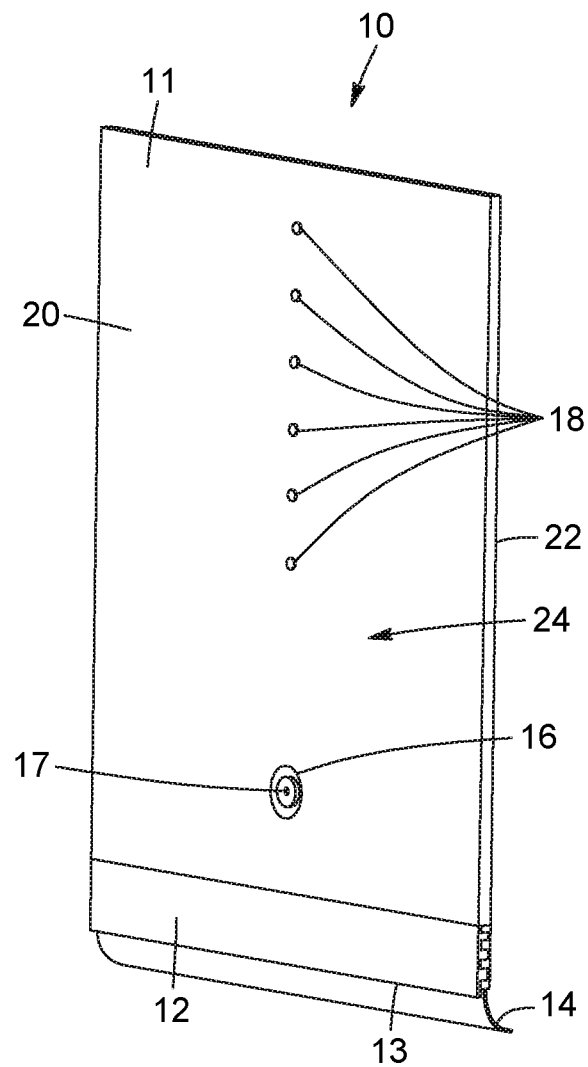
FIG. 2 is a perspective view of the front of the disposal container according to an embodiment of the present invention.

According to an embodiment, the studs 18 are positioned on opposite side walls 20, 22 of the bag 11 to insert a stud into the air extraction aperture 17 upon rolling the bag 11 or folding the bag multiple times, as illustrated on FIGS. 1A and 1B. Alternatively, the one-way degassing valve 16 and one or more of the studs 18 can be positioned on a same side wall 20 of the bag 11 for folding the bag in half and maintaining it in this position as shown on FIG. 2. In some embodiments, studs 18 may be provided on both side walls 20, 22 to provide a choice between folding and rolling the bag.

It will be readily understood that the studs 18 may be sized and shaped as illustrated in the figures, but that in other embodiment the studs may take other forms such as snap-shaped, pin-shaped, etc.

As will be readily understood by one skilled in the art, the distribution of the studs 18 over one or both side walls 20, 22 of the bag 11 provides the user with different options for locking the bag 11 in a compact state. Depending on the size and shape of the soiled undergarment inserted in the bag 11, the user can reconfigure the bag to minimize its size and use the stud closest to the degassing valve 16 after reconfiguration to secure the bag 11 in its new compact state. The user can then more easily conceal the container for transport until a suitable opportunity for disposing of the soiled undergarment arises.

Of course, numerous modifications could be made to the embodiments described above without departing from the scope of the invention as defined in the appended claims.

The invention claimed is:

1. A disposal container for concealing a soiled undergarment, the disposal container comprising:
   a bag having opposite side walls and a top opening for
      inserting the soiled undergarment in the bag therethrough, the top opening being provided with a sealable closure for sealing the bag with the soiled undergarment contained therein; and a resizing mechanism, comprising:

a one-way degassing valve mounted through a first one of said side walls of the bag, said one-way degassing valve having an air extraction aperture configured to extract air from the bag, when sealed, upon application of a force on the bag by a user; and a plurality of studs each sized and shaped to fit into and close the air extraction aperture of the one-way degassing valve, each stud of the plurality of studs being positioned on one of said side walls at a different distance from the top opening of the bag.

2. A disposal container according to claim 1 wherein the one-way degassing valve and the plurality of studs are respectively positioned on opposite ones of said side walls of the bag.

3. A disposal container according to claim 1, wherein the one-way degassing valve and the plurality of studs are positioned on a same one of said side walls of the bag.

4. A disposal container according to claim 1, wherein the studs are positioned along a straight line perpendicular to the top opening of the bag.

5. A disposal container according to claim 4, wherein the studs are equally spaced from one another.

6. A disposal container according to claim 1, wherein the plurality of studs comprises between 2 and 10 of said studs.

7. A disposal container according to claim 1, wherein the side walls of the bag have a rectangular shape.

8. A disposal container according to claim 1, wherein the side walls of the bag are shaped as a mitten.

9. A disposal container according to claim 1, wherein the air extraction aperture and the studs are configured so that the insertion of one of said studs into the aperture produces an audible clicking sound.

10. A disposal container according to claim 1, wherein the bag further comprises an adhesive-covered plastic overlap foldable over the sealable closure of the bag.

11. A disposal container according to claim 1, wherein the bag is made of a disposable material.

12. A disposal container according to claim 11, wherein the disposable material is polyethylene.

* * * * *